United States Patent [19]

Groner

[11] Patent Number: 5,714,362
[45] Date of Patent: *Feb. 3, 1998

[54] HUMAN SUPEROXIDE DISMUTASE CDNA

[75] Inventor: Yoram Groner, Rehovot, Israel

[73] Assignee: Yeda Research and Development Co. Ltd., Rehovot, Israel

[*] Notice: The term of this patent shall not extend beyond the expiration date of Pat. No. 5,196,335.

[21] Appl. No.: 429,203

[22] Filed: Apr. 26, 1995

Related U.S. Application Data

[63] Continuation of Ser. No. 255,560, Jun. 8, 1994, abandoned, which is a continuation of Ser. No. 136,485, Oct. 13, 1993, abandoned, which is a continuation of Ser. No. 6,811, Jan. 21, 1993, abandoned, which is a division of Ser. No. 547,827, Jul. 2, 1990, Pat. No. 5,196,335, which is a continuation of Ser. No. 315,331, Feb. 24, 1989, abandoned, which is a continuation of Ser. No. 726,500, Apr. 24, 1985, abandoned, which is a continuation-in-part of Ser. No. 489,786, Apr. 29, 1983, abandoned.

[30] Foreign Application Priority Data

Apr. 27, 1984 [CA] Canada .................................. 452943

[51] Int. Cl.$^6$ .................................. C12N 1/21; C12N 9/02; C12N 15/53
[52] U.S. Cl. .................................. 435/189; 435/152.3
[58] Field of Search .................................. 435/189

[56] References Cited

U.S. PATENT DOCUMENTS

| | | | |
|---|---|---|---|
| 3,579,495 | 5/1971 | Huber | 435/189 |
| 4,237,224 | 12/1980 | Cohen et al. | 435/69.1 |
| 4,332,892 | 6/1982 | Ptashne et al. | 435/69.7 |
| 4,346,174 | 8/1982 | Yasuda | 435/189 |
| 4,394,443 | 7/1983 | Weissmann et al. | 435/6 |
| 4,435,506 | 3/1984 | Jackson et al. | 435/189 |
| 4,742,004 | 5/1988 | Hartman et al. | 435/189 |
| 4,818,698 | 4/1989 | Sagai et al. | 435/189 |
| 5,196,335 | 3/1993 | Groner | 435/325 |
| 5,240,847 | 8/1993 | Heckl et al. | 435/189 |

FOREIGN PATENT DOCUMENTS 0138111  4/1985  European Pat. Off.

OTHER PUBLICATIONS

Guarante et al., Cell 20:543-553 (1980).
Talmadge et al., Gene 12:235-241 (1980).
Lieman-Hurwitz et al., Proc. Natl. Acad. Sci. USA 79:2808-2811 (1982).
Lieman-Hurwitz et al., Isr. J. Med. Sci. 17(6):477: (1981).
T. Maniatis, et al., *Molecular Cloning: A Laboratory Manual*, Cold Spring Harbor Laboratory, Cold Spring Harbor, New York, pp. 230-240 (1982).
D. Barra et al., Ital. J. Biochem. 31: 28-38 (1982).
M. Houghton, et al., Nucleic Acids Research 8: 2885-2894 (1980).
J. Jabusch, et al., Biochemistry 19: 2310-2316 (1980).
Martini et al., Italian Journal of Biochemistry 31(1):39-47 (1982).
Martin et al., J. Biol. Chem. 256(12):6080-9 (1981) (Exhibit 17).
Barra et al., Biochemical and Biophysical Research Communications 81(4):1195-1200 (1978) (Exhibit 18).
Barra et al., FEBS Letters 120(1):53-56 (1980) (Exhibit 19).
Porter et al., Arch. Biochem. Biophys. 105:319-325 (1964).
Merck Index 10th ed., p. 985 No. 6742 (1983) (Exhibit 21).
Metzler in Biochemistry: The Chemical Reactions of Living Cells, Academic Press, New York, NY pp. 130-131 (1977) (Exhibit 22).
Touati, Journal of Bacteriology 155(3):1078-1087 (1983) (Exhibit 26).
Lin et al., Science 209:285-7 (1980) (Exhibit 28).
Lieman-Hurwitz et al., Biochem. Int. 3(2):107-15 (1981) (Exhibit 29).
Knowles, J., Science 236:1252-1258 (1987) (Exhibit 30).
Fujii, H. et al., J. Biol. Chem. 255(13):6421-6423 (1980) (Exhibit 31).
Wilson, J. et al., J. Clin. Invest. 71(5):1331-1335 (1983) (Exhibit 32).
Moo-Penn, W. et al., Hemoglobin 5(7-8):715-724 (1981) (Exhibit 33).
Wilson, J. et al., J. Bio. Chem. 259(1):27-30 (1984) (Exhibit 34).
Fujii, H. et al., Proc. Natl. Acad. Sci. 78(4):2587-2590 (1981) (Exhibit 35).
Lee, Y. et al., Proc. Natl. Acad. Sci. 78(11):7052-7055 (1981) (Exhibit 36).
Maniatis et al., "Molecular Cloning, A Laboratory Manual", Cold Spring Harbor Laboratory pp. 412-430 (1982) (Exhibit 37).

*Primary Examiner*—Eric Grimes
*Attorney, Agent, or Firm*—John P. White

[57] ABSTRACT

A double-stranded cDNA molecule which includes DNA encoding human cytoplasmic superoxide dismutase has been created. The sequence of one strand of a double-stranded DNA molecule which encodes human cytoplasmic superoxide dismutase has been discovered. Such molecules may be introduced in procaryotic, e.g., bacterial, or eucaryotic, e.g., yeast or mammalian, cells and the resulting cells cultured or grown under suitable conditions so as to produce human cytoplasmic superoxide dismutase which may then be recovered.

2 Claims, 1 Drawing Sheet

FIG. 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|---|---|---|---|---|---|---|---|---|---|
| | ALA | THR | LYS | ALA | VAL | CYS | VAL | LEU | LYS | GLY | ASP | GLY | PRO | VAL | GLN | GLY | ILE | ILE | ASN | PHE | GLU | GLN | LYS | GLU | SER | ASN |
| G₃₂ | ATG, | GCG, | AAG, | GCC, | GTG, | TGC, | GTG, | CTG, | AAG, | GGC, | GAC, | GGC, | CCA, | GTG, | CAG, | GGC, | ATC, | ATC, | AAT, | TTC, | GAG, | CAG, | AAG, | GAA, | AGT, | AAT, |
| | | | | 40 | | | | 50 | | | | 60 | | | | 70 | | | | 80 | | | | 90 | | 100 | 110 |

| 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 |
|---|---|---|---|---|---|---|---|---|---|---|---|---|---|---|---|---|---|---|---|---|---|---|---|---|---|---|
| GLY | PRO | VAL | LYS | VAL | TRP | GLY | SER | ILE | LYS | GLY | LEU | THR | GLU | GLY | LEU | HIS | GLY | PHE | HIS | VAL | HIS | GLU | PHE | GLY | ASP | ASN |
| GGA, | CCA, | GTG, | AAG, | GTG, | TGG, | GGA, | AGC, | ATT, | AAA, | GGA, | CTG, | ACT, | GAA, | GGC, | CTG, | CAT, | GGA, | TTC, | CAT, | GTT, | CAT, | GAG, | TTT, | GGA, | GAT, | AAT, |
| | 120 | | | | 130 | | | | 140 | | | | 150 | | | | 160 | | | | 170 | | | | 180 | 190 |

| 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|
| THR | ALA | GLY | CYS | THR | SER | ALA | GLY | PRO | HIS | PHE | ASN | PRO | LEU | SER | ARG | LYS | HIS | GLY | GLY | PRO | LYS | ASP | GLU | ARG | HIS |
| ACG, | GCA, | GGC, | TGT, | ACC, | AGT, | GCA, | GGT, | CCT, | CAC, | TTT, | AAT, | CCT, | CTA, | TCC, | AGA, | AAA, | CAC, | GGT, | GGG, | CCA, | AAG, | GAT, | GAA, | AGG, | CAT, |
| | 200 | | | | 210 | | | | 220 | | | | 230 | | | | 240 | | | | 250 | | | | 260 | 270 |

| 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|
| VAL | GLY | ASP | LEU | GLY | ASN | VAL | THR | ALA | ASP | LYS | ASP | GLY | VAL | ALA | ASP | VAL | SER | ILE | GLU | ASP | SER | VAL | ILE | SER | LEU | SER |
| GTT, | GGA, | GAC, | TTG, | GGC, | AAT, | GTA, | ACT, | GCT, | GAC, | AAA, | GAT, | GGT, | GTG, | GCC, | GAT, | GTG, | TCT, | ATT, | GAA, | GAT, | TCT, | GTG, | ATC, | TCA, | CTC, | TCA, |
| | 280 | | | | 290 | | | | 300 | | | | 310 | | | | 320 | | | | 330 | | | | 340 | 350 |

| 108 | 109 | 110 | 111 | 112 | 113 | 114 | 115 | 116 | 117 | 118 | 119 | 120 | 121 | 122 | 123 | 124 | 125 | 126 | 127 | 128 | 129 | 130 | 131 | 132 | 133 | 134 |
|---|---|---|---|---|---|---|---|---|---|---|---|---|---|---|---|---|---|---|---|---|---|---|---|---|---|---|
| GLY | ASP | HIS | CYS | ILE | ILE | GLY | ARG | THR | LEU | VAL | VAL | HIS | GLU | LYS | ALA | ASP | ASP | LEU | GLY | LYS | GLY | GLY | ASN | GLU | GLY | SER |
| GGA, | GAC, | CAT, | TGC, | ATC, | ATT, | GGG, | CGC, | ACA, | CTG, | GTC, | GTC, | CAT, | GAA, | AAA, | GCA, | GAT, | GAC, | TTG, | GGC, | AAA, | GGT, | GGA, | AAT, | GAA, | GAA, | AGT, |
| | 360 | | | | 370 | | | | 380 | | | | 390 | | | | 400 | | | | 410 | | | | 420 | 430 |

| 135 | 136 | 137 | 138 | 139 | 140 | 141 | 142 | 143 | 144 | 145 | 146 | 147 | 148 | 149 | 150 | 151 | 152 | 153 |
|---|---|---|---|---|---|---|---|---|---|---|---|---|---|---|---|---|---|---|
| THR | LYS | THR | GLY | ASN | ALA | GLY | SER | ARG | LEU | ALA | CYS | GLY | VAL | ILE | GLY | ILE | ALA | GLN | STOP |
| ACA, | AAG, | ACA, | GGA, | AAC, | GCT, | GGA, | AGT, | CGT, | TTG, | GCT, | TGT, | GGT, | GTA, | ATT, | GGG, | ATC, | GCC, | CAA, | TAAACATTCCCCTTGGATGTAGTCTGAG |
| | 440 | | | | 450 | | | | 460 | | | | 470 | | | | 480 | 490 | 500 510 520 |

GCCCTTAACTCATCTGTTATCCTGCTAGCTGTAGAAATGTATCCTGATAAACATTAAACACTGTAATCTTAAAAAAAAAAAC₁₇
530  540  550  560  570  580  590  600

HUMAN SUPEROXIDE DISMUTASE CDNA

This application is a continuation of U.S. Ser. No. 08/255,560, filed Jun. 8, 1994, now abandoned; which is a continuation of U.S. Ser. No. 08/136,485, filed Oct. 13, 1993, now abandoned; which is a continuation of U.S. Ser. No. 08/006,811, filed Jan. 21, 1993, now abandoned; which is a divisional of U.S. Ser. No. 07/547,827, filed Jul. 2, 1990, now U.S. Pat. No. 5,196,335, issued Mar. 23, 1992; which is a continuation of U.S. Ser. No. 07/315,331, filed February 24, 1989, now abandoned; which was a continuation of U.S. Ser. No. 06/726,500 filed Apr. 24, 1985, now abandoned; which was a continuation-in-part of Ser. No. 06/489,786, filed Apr. 29, 1983, now abandoned.

BACKGROUND OF THE INVENTION

Throughout this application various publications are referenced by arabic numerals within parentheses. Full citations for these references may be found at the end of the specification immediately preceding the claims. The disclosures of these publications in their entireties are hereby incorporated by reference into this application in order to more fully describe the state of art as known to those skilled therein as of the date of the invention described and claimed herein.

Superoxide dismutase (superoxide:superoxide oxidoreductase, EC 1.15.1.1) is the enzyme that catalyzes the removal of superoxide radicals, which are generated in a variety of biological oxidations (1). It provides a defense against oxygen toxicity and damage than may be caused to cells by carcinogenic hydrocarbons (1). The human Cu—Zn superoxide dismutase (SOD-1) is a dimeric protein composed of apparently identical noncovalently linked subunits, each with a molecular weight of 16,000–19,000 (2,3). The locus for human cytoplasmic superoxide dismutase (SOD-1) was assigned to chromosome 21 (4).

About 1 in 600 newborn babies carries an extra chromosome 21, a condition technically known as trisomy 21 or Down syndrome (5,6). This chromosome imbalance is a known cause of spontaneous abortion and mental retardation (5). In most cases, the patients with Down syndrome have karyotypes with 47 chromosomes (46 plus one additional 21). However, cases of Down syndrome in which only a portion of chromosome 21 is present in triplicate have enabled the localization of the "responsible" region to segment 21q22, the distal portion of the long arm (7–11). Although trisomy 21 was identified as a human genetic disease over 20 years ago (5), little is known about the mechanisms by which the extra chromosome or the extra chromosomal segment 21q22 results in reduced viability and abnormalities of morphogenesis and mental function. It is generally assumed that the extra chromosome or chromosomal segment codes for normal products and that the abnormalities found in Down syndrome are produced by an imbalance due to changes in gene dosage (12). Namely, the presence of additional genetic material in the cell will result in the production of commensurately increased amounts of the gene products coded by the extra chromosomal segment. Indeed, Down syndrome patients show an increase of about 50% in SOD-1 activity (13–15) due to a higher level of SOD-1 protein (16). However, it is not known whether this gene dosage phenomenon is a result of quantitative changes in the amount of SOD-1 mRNA.

In the past, most of the reports on Down syndrome involved family karyotyping and clinical studies of the effects of the disease on patients. It is only recently that recombinant DNA techniques have enabled one to approach the molecular biology of the chromosomal region involved and try to gain insight into the mechanism by which abnormal karyotypes result in abnormal phenotype.

Superoxide dismutase is also of interest because of its pharmacological properties. Bovine-derived superoxide dismutase (orgotein) has been recognized to possess antiinflammatory properties and is currently marketed in parts of Europe as a human pharmaceutical. It is also sold in United States as a veterinary product, particularly for use with horses. However, supplies of orgotein are limited. Prior techniques involving recovery from bovine or other animal cells have serious limitations and the orgotein so obtained may produce allergic reactions in humans because of its non-human origin.

To meet these various needs, efforts were undertaken to identify the gene encoding human cytoplasmic superoxide dismutase and to prepare a cDNA molecule containing such a gene. These efforts resulted in the present invention which is described more fully hereinafter. A description of certain aspects of the invention was published in Proc. Natl. Acad. Sci., USA, vol. 79, pp. 2808–2811, May 1982 (30).

SUMMARY OF THE INVENTION

A double-stranded cDNA molecule which includes DNA encoding human cytoplasmic superoxide dismutase has been made. The nucleotide sequence of one strand of a double-stranded DNA molecule which encodes human cytoplasmic superoxide dismutase has been discovered and is shown in FIG. 1.

The double-stranded cDNA molecule or any other double-stranded DNA molecule which contains a nucleotide strand having the sequence shown in FIG. 1 may be incorporated into a cloning vehicle such as a plasmid or virus. Either DNA molecule may be introduced into a cell, either procaryotic, e.g., bacterial, or eucaryotic, e.g., yeast or mammalian, using known methods, including but not limited to methods involving cloning vehicles containing either molecule.

Cells into which such DNA molecules have been introduced may be cultured or grown in accordance with methods known to those skilled in the art under suitable conditions permitting transcription of the DNA into mRNA and expression of the mRNA as protein. The resulting protein may then be recovered.

BRIEF DESCRIPTION OF THE DRAWING

FIG. 1 shows the nucleotide sequence of one strand of a double-stranded DNA molecule encoding human cytoplasmic superoxide dismutase.

DETAILED DESCRIPTION OF THE INVENTION

A double-stranded cDNA molecule which includes DNA encoding human cytoplasmic superoxide dismutase has been made. The nucleotide sequence of one strand of a double-stranded DNA molecule which encodes human cytoplasmic superoxide dismutase has been discovered. This sequence is shown in FIG. 1. The methods of preparing the cDNA and of determining the sequence of DNA encoding the human superoxide dismutase are known to those skilled in the art and are described more fully hereinafter under Experimental Details. Moreover, now that the DNA sequence which encodes the superoxide dismutase has been discovered, known synthetic methods can be employed to prepare DNA molecules having or including portions which have the sequence.

Conventional cloning vehicles such as plasmids, e.g., pBR322, viruses or bacteriophages, e.g., λ, can be modified or engineered using known methods so as to produce novel cloning vehicles which contain cDNA encoding human cytoplasmic superoxide dismutase. Similarly, such cloning vehicles can be modified or engineered so that they contain DNA molecules, one strand of which includes a segment having the sequence shown in FIG. 1. The DNA molecule inserted may be made by various methods including enzymatic or chemical synthesis.

The resulting cloning vehicles are chemical entities which do not occur in nature and may only be created by the modern technology commonly described as recombinant DNA technology. These cloning vehicles may be introduced in cells, either procaryotic, e.g., bacterial (*E. coli., B. subtilis*, etc.) or eucaryotic, e.g., yeast or mammalian, using techniques known to those skilled in the art, such as transformation, tranfection and the like. The cells into which the cloning vehicles are introduced will thus contain cDNA encoding human cytoplasmic superoxide dismutase if the cDNA was present in the cloning vehicle or will contain DNA which includes a strand, all or a portion of which has the sequence shown in FIG. 1 if such DNA was present in the cloning vehicle.

The resulting cells into which DNA encoding human cytoplasmic superoxide dismutase has been introduced may be grown or cultured as appropriate under suitable conditions known to those skilled in the art so as to effect expression of the genetic information encoded by the DNA and production of the dismutase which may then be recovered.

Experimental Details

Materials and Methods

Materials. Reverse transcriptase (RNA-dependent DNA polymerase) from arian myeloblastosis virus was kindly supplied by Joseph Beard (Life Science, Gulfport, Fla.). Nuclease S1 and calf thymus terminal deoxynucleotidyl-transferase were purchased from Miles and P-L Biochemicals, respectively. Restriction enzymes were purchased from New England BioLabs and were used according to the supplier's instructions. Nitrocellulose membrane filter (0.45-µm pore diameter) was obtained from Schleicher & Schuell. Labeled nucleotides were from the Radiochemical Centre (Amersham, England).

Cells. The trisomy 21 skin fibroblast culture is derived from a 1-month-old male and was obtained from the Human Genetic Cell Repository (Camden, N.J.), culture no. GM-2504. The SV80 cells are a continuous line of simian virus 40-transformed human fibroblasts (17). The mouse-human hybrid cell line WAVR4dF9–4a (18) originating from the fusion of a mouse A9 cell and a human diploid fibroblast was obtained from F. Ruddle. It contains a full mouse genome plus human chromosome 21. The FS-11 cells are human fibroblasts from foreskins, established by D. Gurar-iRotman (19).

Construction of cDNA Clones. A poly(A)-containing RNA fraction enriched for SOD-1 mRNA was isolated as described (3). Briefly, total poly(A)-containing RNA was prepared from SV80 cells and fractionated through a linear sucrose gradient. Fractions were assayed for mRNA encoding SOD-1 by in vitro translation and immunoprecipitation. The fraction containing SOD-1 mRNA (≈11S) was used for the synthesis of double-stranded (ds) DNA according to the procedure of Wickets et al. (20). ds cDNAs were introduced into the Pst I site of pBR322 by using the dG.dC tailing and hybridization protocol of Villa-Komaroff et al. (21). The chimeric molecules were used to transform *Escherichia coli* strain HB101 in the presence of $CaCl_2$ (22). Transformants that were tetracycline resistant were screened by in situ colony hybridization (23). Selection of mRNA by hybridization was performed as described by Ricciardi et al. (24). Cell-free translation in rabbit reticulocyte lysate, immunoprecipitation, and $NaDodSO_4$/polyacrylamide gel electrophoresis were carried out as described (3). Plasmid DNA was isolated from chloramphenicol-amplified cultures by Triton X-100 lysis (25) and was purified on CsCl/ethidium bromide gradients. All experiments with recombinant plasmids were performed in accordance with the National Institutes of Health guidelines for recombinant DNA research.

Blot Hybridization. Hybridization of DNA with filter-bound RNA was carried out by using essentially the method described by Thomas (26).

Heteroduplex and R-Loop Formation. Plasmid DNAs (0.06 µg were digested with EcoRI, denatured for 10 min in 0.1M NaOH/12mMEDTA, and neutralized by adjusting the solution to 160mM Tris.HCl, pH 8.5/400mM $NaClO_4$. Formamide (recrystallized three times) was added to 50% (vol/vol) and renaturation was allowed to proceed at 37° C. for 6 min. R-loops were prepared as described by Brack (27).

cDNA Sequence. DNA was sequenced using the chemical method described by Maxam and Gilbert (20).

Results

Construction of cDNA Clones and Translational Analysis. An earlier study (3) established that mRNA that codes for human SOD-1 sediments at 11S in linear sucrose gradients and can be translated in vitro to an immunoprecipitable polypeptide of 19,000 $M_r$. This fractionation procedure was applied to obtain partially purified SOD-1 mRNA. A sucrose gradient fraction enriched for SOD-1 mRNA (≈2 µg) was copied into ds cDNA and cloned in *E. coli* as described in Materials and Methods. Plasmid (200–500 ng) containing ds SOD-1 DNA was used for transformation and 20,000 transformed colonies with tetracycline resistant ampicillin-sensitive phenotype were obtained. Three thousand transformants were replated in duplicate and screened for recombinants by in situ hybridization (23), using [$^{32}$P]DNA complementary to the mRNA used for generating cloned material. Significant hybridization was detected in 300 of the 3,000 colonies analyzed. Seventy-five of the resultant positive colonies were selected on the basis of signal strength for further analysis by hybridization selection and cell-free translation (3, 24). Plasmid DNA, purified from individual colonies and immobilized onto nitrocellulose filters, was used to select mRNA by hybridization. The bound RNA was eluted and translated in a cell-free system. Translation products were immunoprecipitated by anti-SOD-1serum and subjected to gel electrophoresis. Out of the 75 clones selected for testing by the "mRNA-fishing translation" procedure, one was found to be positive. The eluted mRNA directed the synthesis of immunoprecipitable 19,000 $M_r$ polypeptides that comigrated with in vivo labeled SOD-1. Two other recombinant plasmids and the vector did not yield any immunoprecipitable proteins. Translation of mRNA from the enriched fraction, but before hybridization, showed a few protein bands after immunoprecipitation, one comigrating with SOD-1. By comparison, it is estimated that ≈30% of the input SOD-1 mRNA was recovered in an active form after the hybridization elution procedure with the filter-bound positive plasmid. This plasmid was named pS61–10.

From the 3,000 clones picked and replated, one more positive clone (designated pS58-13) was identified by colony hybridization using the cDNA insert of pS61-10 as a probe. Therefore, the overall frequency of SOD-1 positive clones was 0.06%.

Characterization of pS61-10. A restriction map of the pS61-10 cDNA insert was prepared. Pst I sites were reconstituted at both ends. The cDNA insert excised from the plasmid by Pst I is 650 bases in length. It was isolated and labeled with [$\alpha$-$^{32}$P]dCTP by using DNA polymerase (large fragment), digested with a series of restriction endonucleases, and fractionated on 2% agarose gels. The insert contained cleavage sites for the enzymes Mbo II, Taq I, Hae III, Alu I, Sau3AI, HinfI, and Ava II. Some of them were mapped by double digestion. The orientation of the insert with respect to the neighboring pBR322 sequences was determined by digesting pS61-10 with Hha I, eluting the 987-bp fragment, and subjecting it to secondary digestion by each of the following enzymes: Alu I, Sau3AI, HinfI, Ava II, and Taq I. Other enzymes did not cleave; these included: Hae II, Hpa II, Bcl I, Hha I, Sac I, Sac II, Bgl II, Kpn I, Hpa I, Xho I, Sma I, Xba I, Bal I, EcoRI, Cla I, HindIII, Pva II, and Sal I.

The size and orientation of the insert cDNA were also analyzed by electron microscopic studies. Plasmid DNAs of pS61-10 and pBR322 were made linear with EcoRI, for which there are no sites within the insert, and they reassociated to form heteroduplex molecules.

All heteroduplexes contained a deletion loop of 650±20 bp at ≈700 bp from one end of the duplex that maps at the Pst I insertion site. This result was in good agreement with the length determined by agarose gel electrophoresis. R-loop structures were obtained by annealing linear pS61-10 DNA (cut with EcoRI) with poly(A)-containing SOD-1 mRNA isolated from SV80 cells and purified by fractionation on a sucrose gradient. The R-loops are located between short and long segments of duplex DNA and in some cases free tails are recognizable at the fork close to the short fragment. It is assumed that the tails represent nonhybridized poly(A) sequences and thus the SOD-1 insert is in an opposite orientation to the β-lactamase gene.

Detection of SOD-1 mRNA in Human and Mouse Cells

Total cytoplasmic poly(A)-containing RNA was isolated from different cell cultures: FS-11 human fibroblasts, SV80 human transformed cell line, WAVR4dF9-4a mouse-human hybrid cell line, and A9 mouse cell line, which is the parent of the hybrid line. These RNAs were treated with formaldehyde and electrophoresed on 1.5% agarose gels containing 6% (vol/vol) formaldehyde as described in Materials and Methods (26). The RNA was transferred to nitrocellulose filters and then hybridized to 32P-labeled cloned SOD-1 cDNA (pS61-10). Two distinct size classes of SOD-1 RNA were detected in RNA extracted from the two human cells and the human-mouse hybrid line. These had molecular lengths (in nucleotides) of 700±50 and 500±50. In RNA extracted from the mouse cell line A9 only the lower band was detected plus an additional very high molecular weight band (≈4,800 nucleotides). The presence of the 700-nucleotide SOD-1RNA in poly(A)-containing RNA extracted from the human-mouse hybrid cell line signified that this class is also coded by human chromosome 21, because this is the only human chromosome present in this hybrid line (18). On the other hand, the 500-nucleotide SOD-1 species is encoded by both the human and mouse chromosomes present in the hybrid line, as evident from the relatively higher amounts of this band. The size of human SOD-1 mRNA has previously been determined by in vitro translation of fractions along a CH$_3$HgOH agarose gel to be ≈420 nucleotides (3). Therefore it was assumed that the 500±50 nucleotide RNA species detected corresponds to the in vitro translatable mRNA.

DISCUSSION

The preceding description concerns the synthesis, cloning, identification and sequencing of a 650-bp cDNA bearing the sequence of human SOD-1 mRNA. Two size classes of human SOD-1 mRNA were identified, with ≈500 and ≈700 nucleotides. Therefore it was assumed that the cDNA inserts of pS61-10 and pS58-13 that are relatively large (650 bp) contain most, if not all, of the mRNA sequences. The two cloned inserts seem similar because their restriction maps were identical and the heteroduplex analysis demonstrated a stable heteroduplex between them throughout the inserts.

As mentioned under Background of the Invention, cytogenetic analysis of mentally retarded patients has shown that trisomy of a small segment of chromosome 21—i.e., band 21q22—is sufficient to result in the phenotype of Down syndrome. More recently a normal SOD-1 activity was found in partial trisomy 21 (28), which suggests that translocation of the 21q22 chromosomal segment can reduce or even abolish SOD-1 expression. It is believed that identification of the genes residing in this chromosomal segment, as well as detailed analysis of their organization, is of great importance in understanding the role differential gene expression (as in cases of gene dosage effects) plays in the phenotype differentiation. The gene locus of SOD-1 is located in the chromosomal band 21q22. It can therefore serve as a starting point for "chromosome walking" along the segment involved in Down phenotype and provide information about the linkage and expression of this gene and its neighbors.

Use of the Human SOD-1 cDNA Clone for Isolation of Plant SOD-1Gene in Order to Construct a Paraquat Resistant Plant Containing Recombinant DNA.

Plant and animal cells have a common way to defend themselves from the destructive oxygen radical $O_2^-$. They contain an enzyme, superoxide dismutase (SOD) which eliminates this radical. There are several types of SOD but the major one termed SOD-1 is almost identical in both animals and plants and its genetic code (i.e. base sequence in the respective DNA fragment) is expected to be quite similar.

Compounds which can be reduced within cells, and whose reduced forms react rapidly with dioxygen ($O_2$), have the potential of diverting intracellular electrons and thus of increasing the production of superoxide ($O_2^-$, a reduced form of oxygen) and of $H_2O_2$ (hydrogen peroxide). In green organisms, the electron source necessary for such processes appears to be photosystem I (PSI). Paraquat, diquat and many other chemicals of the bipyridillium group, and some other molecules (i.e. plumbagin, juglone, pycocyanine and streptonigrin are among the compounds shown to exhibit this behavior.

Paraquat is a non-selective herbicide, killing all photosynthesizing cells without leaving chemically active residues in or above the ground. Therefore, it does not damage the oncoming crop, or infest the growing medium, and does not allow selection for resistance in weeds. Since its introduction, this weed-killer is used world-wide as a herbicide. Its use is growing continuously with the increasing popularity of the no-till agrotechnique, where it is used to eradicate existing vegetation prior to crop sowing or to its emergence. This chemical could serve as an efficient weed-killer in postemergence stages providing that the crop plants would be tolerant to its toxic effect.

Owing to its high and general toxicity to green plants, its quite fast action, and its non-residual nature, it would not be expected that tolerance to PQ would develop in the field. However, due to it being applied several times every year in certain areas, several resistant genotypes have been uncovered. In the four known plants, it was found that these resulted from an excessive unadvisable overuse of the herbicide. The examined resistant types contained significantly higher levels of SOD activity than the original populations (i.e. ryegrass). The benefits from having a paraquat tolerant crop are obvious. PQ tolerance was transferred to commercial cultivar of ryegrass from the resistant type, using classical plant breeding techniques. The resulting new variety is sufficiently resistant to the herbicidal application, surviving treatment with PQ in the field.

The cDNA clone for human SOD-1 was used to identify the plant DNA segment which carries the SOD-1 gene. Total DNA was digested with Eco RI. 20 g of digested human DNA and plant DNA were placed on 0.8% agarose gel. After electrophoresis DNA was transferred to nitrocellulose and hybridized to 32P-labeled probe of human SOD-1 cDNA. It was seen that the radiolabeled DNA probe prepared from the human cDNA clone reacted with plant SOD-1 gene, providing a means for specifically detecting the plant gene and for rapid isolation and cloning of the gene. The isolated plant gene may be inserted into various known expression vectors which provide maximum expression and introduced into plant cells.

REFERENCES

1. Fridovich, I. (1975) Annu. Rev. Biochem. 44, 147–159.
2. Hartz, J. W. & Deutsch, F. H. (1972) J. Biol. Chem. 247, 7043–7050.
3. Lieman-Hurwitz, J., Wolf, D., Goldman, D. & Groner, Y. (1981) Biochem. Int. 3, 107–115.
4. Tan, Y. H., Tischfield, J. & Ruddle, F. H. (1973) J. Exp. Med. 137, 317–330.
5. Lejeune, J. M., Gautier, M. & Turpin, R. (1959) C. R. Acad. Sci. 248, 1721–1722.
6. Smith, G. F. & Burg, J. M. (1976) in Down's Anomaly (Churchill Livingston, Edinburgh), pp. 234–251.
7. Paris Conference 1971: Standardization in Human Cytogenetics. Birth Defects: Original Article Series 8 (1972) (The National Foundation, New York), Vol. 7.
8. Niebuhr, E. (1974) Humangenetik 21, 99–101.
9. Hagemeijer, A. & Smit, E. M. E. (1977) Hum. Genet. 38, 15–23.
10. Williams, J. D., Summit, R. L., Martens, P. R. & Kimbrell, R. A.(1975) Am. J. Hun. Genet. 27, 478–485.
11. Sinet, P. M., Couturier, a., Dutrillaux, B., Poissonnier, M., Rauol, 0., Rethore, M., Allard, D., Lejeune, J. & Jerome, H. (1976) Exp. Cell Res. 97, 47–55.
12. Kurnit, D. M. (1979) Proc. Natl. Acad. Sci. USA 76, 2372–2375.
13. Sichitiu, S., Sinet, P. M., Lejeune, J. & Frezal, J. (1974) Humangenetik 23, 65–72.
14. Crosti, N., Sera, A., Rigo, A. & Viglino, P. (1976) Hum. Genet. 31, 197–202.
15. Feaster, W. W., Kwok, L. W. & Epstein, C. J. (1977) Am. J. Hum. Genet. 29, 563–570.
16. Frants, R. R., Eriksson, A. W., Jongbloet, P. H. & Hamers, A. J. (1975) Lancet ii, 42–43.
17. Todaro, G. J., Green, H. & Swift, C. (1966) Science 153, 1252–1254.
18. Kozak, C. A., Lawrence, J. B. & Ruddle, F. H. (1977) Exp. Cell Res. 105, 109–117.
19. Weissenbach, J., Zeevi, M., Landau, T. & Revel, M. (1979) Eur. J. Biochem. 98, 1–8.
20. Wickens, M. P., Buell, G. N. & Schimke, R. T. (1978) J. Biol. Chem. 253, 2483–2495.
21. Villa-Komaroff, L., Efstratiadis, A., Broome, S., Lomedico, P., Tizard, R., Naber, S. P., Chick, W. L. & Gilbert, W. (1978) Proc. Natl. Acad. Sci. USA 75, 3727–3731.
22. Kushner, S. R. (1978) in Genetic Engineering, eds. Boyer, H. W. & Nicosia, S. (Elsevier/North-Holland, N.Y.), pp. 17–23.
23. Grunstein, M. & Hogness, D. S. (1975) Proc. Natl. Acad. Sci. USA 72, 3961–3965.
24. Ricciardi, R. P., Miller, J. S. & Roberts, B. E.(1979) Proc. Natl. Acad. Sci. USA 76, 4927–4931.
25. Lovett, M. A., Guiney, D. G. & Helinski, D. R. (1974) Proc. Natl. Acad. Sci. USA 71, 3854–3857.
26. Thomas, P.S. (1980) Proc. Natl. Acad. Sci. USA 77, 5201–5205.
27. Brack, C. (1981) Crit. Rev. Biochem. 10, 113–169.
28. Mattei, J. F., Mattei, M. G., Baeteman, M. A. & Girand, F. (1981) Hum. Genet. 56, 409–411.
29. Maxam, S. M. & Gilbert, W. (1980) in *Methods in Enzymology*, eds. Grossman, L. & Moldave, K., (Academic Press, New York) vol. 65, pp. 499–560.
30. Lieman-Hurwitz, J., Dafni, N., Lavie, V. & Groner, Y. (1982) Proc. Natl. Acad. Sci. USA 79, 2808–2811.

What is claimed is:

1. A method of producing human cytoplasmic Cu—Zn superoxide dismutase which comprises culturing or growing a cell into which a cDNA molecule which comprises DNA encoding human cytoplasmic Cu—Zn superoxide dismutase has been introduced, under suitable conditions permitting expression of the DNA encoding the superoxide dismutase and recovering the superoxide dismutase so produced.

2. A method of producing human Cu—Zn superoxide dismutase which comprises culturing or growing a cell into which a double stranded cDNA molecule which encodes human Cu—Zn superoxide dismutase, one strand of which comprises the nucleotide sequence shown in FIG. 1 has been introduced under suitable conditions permitting expression of DNA encoding the superoxide dismutase and recovering the Cu—Zn superoxide dismutase so produced.

* * * * *